United States Patent [19]

Brimhall

[11] Patent Number: 5,498,247
[45] Date of Patent: Mar. 12, 1996

[54] ELASTIC PLUG ASSEMBLY FOR MEDICAL DEVICE

[75] Inventor: Greg L. Brimhall, West Jordan, Utah

[73] Assignee: Becton Dickinson and Company, Franklin Lakes

[21] Appl. No.: 364,636

[22] Filed: Dec. 27, 1994

[51] Int. Cl.⁶ ................................................. A61M 5/00
[52] U.S. Cl. ..................... 604/244; 604/256; 604/284
[58] Field of Search ................................ 604/236, 238, 604/244, 256, 264, 284, 905; 215/355

[56] References Cited

U.S. PATENT DOCUMENTS

| | | | |
|---|---|---|---|
| 2,847,995 | 8/1958 | Adams | 604/905 |
| 4,294,249 | 10/1981 | Sheehan et al. | 215/355 |
| 4,673,394 | 1/1987 | Fenton, Jr. et al. | 604/236 |
| 5,232,109 | 8/1993 | Tirrell et al. | 215/355 |
| 5,279,571 | 1/1994 | Larkin | 604/256 |
| 5,300,034 | 4/1994 | Behnke et al. | 604/256 |
| 5,342,316 | 8/1994 | Wallace | 604/905 |
| 5,403,293 | 4/1995 | Grabenkort | 604/256 |

Primary Examiner—Corrine M. Maglione
Assistant Examiner—Michael L. Arness
Attorney, Agent, or Firm—Eric M. Lee

[57] ABSTRACT

An elastic plug assembly is provided for selective penetration by a needle. The elastic plug assembly comprises an elastic plug that is retained in a radially compressed state by a rigid plug retainer. The combined elastic plug and rigid plug retainer may be secured in a housing formed from an elastomeric material. The elastic plug may be penetrated by a needle. Upon removal of the needle, the radially compressed elastic plug will be urged toward its compressed condition with the space that had been occupied by the needle being completely filled to effectively achieve the sealing function of the plug. Needles may repeatedly be penetrated through the plug and removed as necessary, and the plug will efficiently return to its substantially solid sealed state after each successive needle removal.

3 Claims, 3 Drawing Sheets

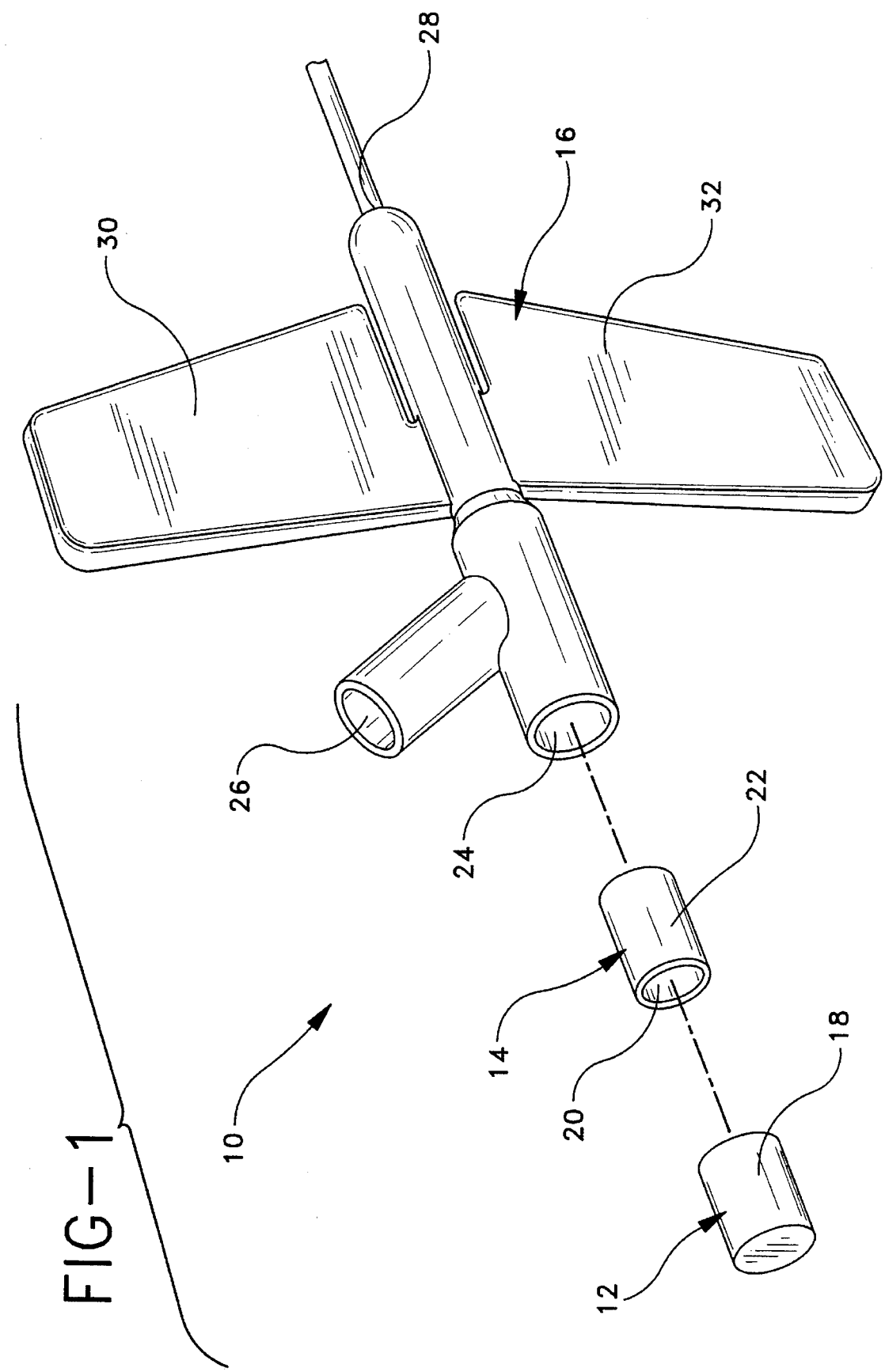

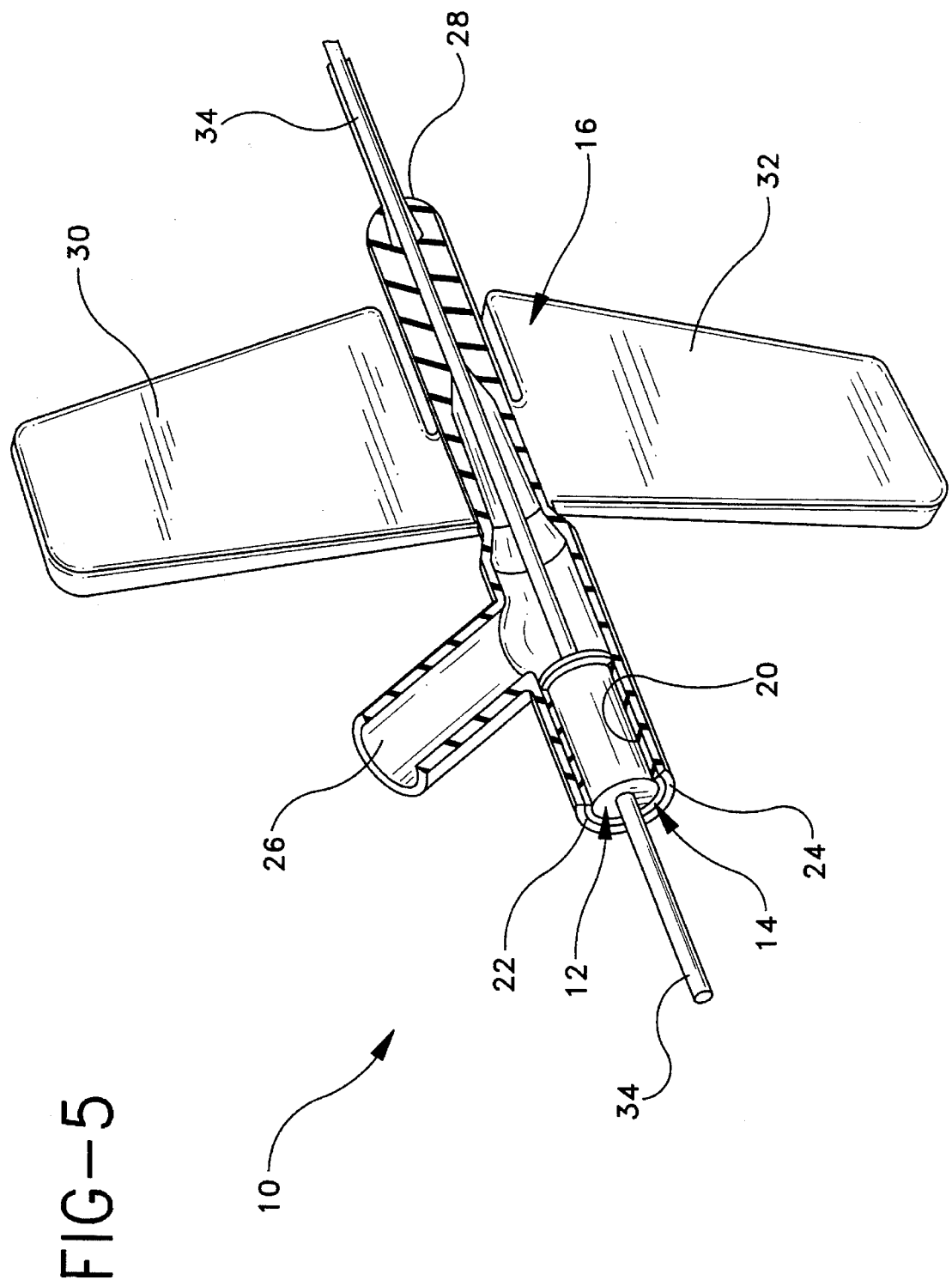

ELASTIC PLUG ASSEMBLY FOR MEDICAL DEVICE

BACKGROUND OF THE INVENTION

This invention relates to an elastic plug assembly for use on a medical device, such as a catheter, that can be penetrated by a needle and that will reseal after removal of the needle. This invention is particularly adapted for use on a catheter having a Y-site connector. Although this invention will be discussed in connection with a catheter having a Y-site connector, it is to be understood that this invention may be used in conjunction with any device which requires a needle to pass through an elastic member that must reseal when the needle is removed.

Intravenous catheters may have Y-site connectors connected to their proximal end to allow first and second flows of liquids into a patient. The first inlet of a Y-site connector may be sealed with an elastic plug that can be penetrated by a needle to allow a healthcare worker to inject liquid such as medication into the patient when needed. The second inlet to the Y-site connector may be placed in communication with another liquid such as a standard saline solution to provide a continual flow of fluid to a patient. The needle passing through the elastic plug in the first inlet is removed after the proper dosage of medication is provided to the patient. If multiple doses of medication are required, the health care worker may subsequently cause a needle to be penetrated through the elastic plug of the Y-site connector to continue the delivery of medication.

Prior art plugs generally perform well. However, it has been found that the material of these plugs may take a set to the needle, particularly if the needle remains in the plug for a considerable period of time. Thus, when the needle is removed from the plug, a hole in the plug remains where the needle had been. Subsequent needles penetrated through the plug are unlikely to enter the small hole left by the previous needle. Thus, the small hole will remain in communication with ambient atmosphere and can cause leakage, evaporation or contamination. Any contamination that may result typically will be caused by ambient atmosphere communicating with either the liquid being administered or with bodily fluids. However, a possibility may exist for bodily fluids escaping through the hole in the elastic plug to contaminate people working in or near the patient to whom the Y-site connector is connected. The potential for these problems becomes greater each time a needle is removed and replaced, since the number of holes remaining in the elastic plug will increase. This problem is encountered not only with Y-site connectors, but in other situations where elastic plugs are periodically penetrated by needles.

SUMMARY OF THE INVENTION

It is therefore an object of this invention to provide an elastic plug assembly for a medical device such as a catheter that can be penetrated by a needle and that will not leak after the needle has been withdrawn.

The elastic plug assembly of this invention includes an elastic plug that is held in compression by a rigid plug retainer. The rigid plug retainer in turn may be held captive within an elastic material that may function as the catheter hub. The elastic plug and the rigid plug retainer both may be substantially cylindrical. The rigid plug retainer preferably defines a cross-sectional dimension of between 60% and 85% of the non-compressed cross-sectional dimension of the elastic plug. Thus, the elastic plug must be radially compressed by approximately 15%–40% for insertion into the rigid plug retainer.

The above and any other objects and advantages of the invention will be apparent upon consideration of the drawings and the following detailed description.

BRIEF DESCRIPTION OF THE DRAWINGS

The preferred embodiments are illustrated in the drawings in which like reference numerals refer to like elements and in which:

FIG. 1 is an exploded perspective view of the elastic plug assembly of this invention in conjunction with a Y-site connector on an intravenous catheter;

FIG. 5 is a perspective view, partly in section, of the elastic plug assembly of this invention in conjunction with a Y-site connector on an intravenous catheter.

DETAILED DESCRIPTION OF THE PREFERRED EMBODIMENT

Figure 4:
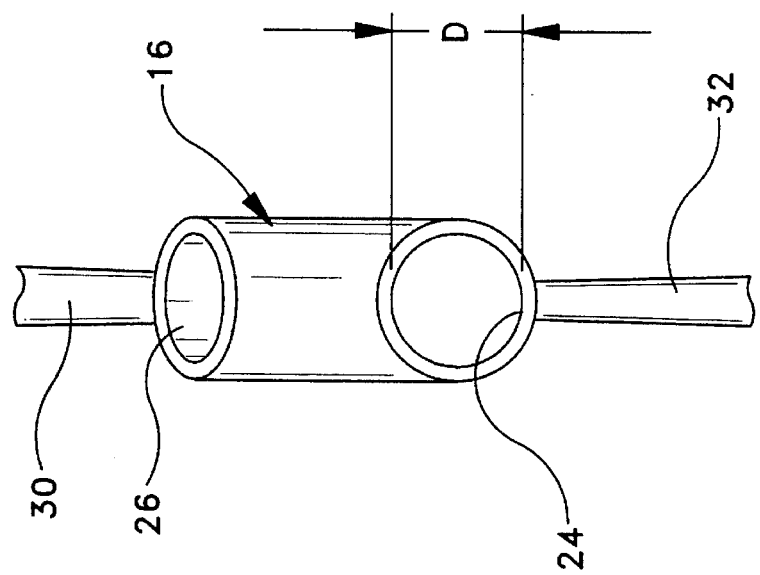
FIG. 4 is an end elevational view of the catheter hub shown in FIG. 1.

An elastic plug assembly in accordance with the subject invention is identified generally by the numeral 10 in FIGS. 1 and 5. Elastic plug assembly 10 includes an elastic plug 12, a rigid plug retainer 14 and a catheter hub 16.

Figure 2:
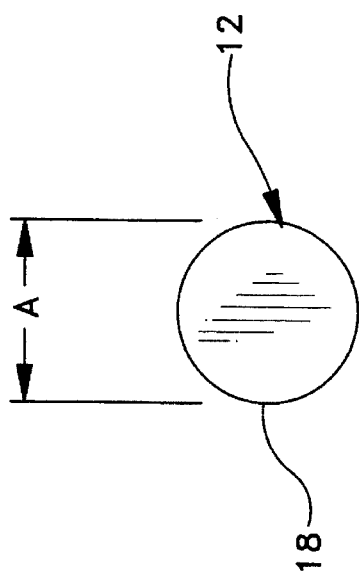
FIG. 2 is an end elevational view of the elastic plug shown in FIG. 1.
Figure 3:
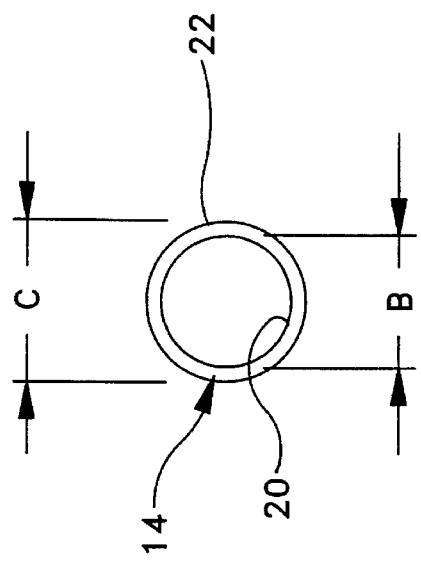
FIG. 3 is an end elevational view of the rigid plug retainer shown in FIG. 1.

With reference to FIGS. 1 and 2, plug 12 is formed from an elastomeric material to define a solid cylinder with an outer cylindrical surface 18 defining a diameter "A". Polyisoprene or latex could be used to form plug 12. Preferably, polyisoprene is used. Plug retainer 14 is formed from a non-elastic rigid material and defines a tubular cylinder with an inner cylindrical surface 20 and an opposed outer cylindrical surface 22. Polycarbonate, ABS or stainless steel could be used to form plug retainer 14. Preferably, stainless steel is used. Inner cylindrical surface 20 of plug retainer 14 has an inside diameter "B" selected such that "B" approximately equals 60% to 85% of diameter "A." Outer cylindrical surface 22 of plug retainer 14 defines an outside diameter "C".

Catheter hub 16 is formed from an elastomeric material such as polyurethane and includes a first inlet 24, a second inlet 26 and an outlet 28 that extends to the catheter cannula. First inlet 24 and outlet 28 are substantially collinear with one another to facilitate passage of a needle continuously through catheter hub 16, as shown in FIG. 5. Catheter hub 16 further includes a pair of flexible planar wings 30 and 32 projecting outwardly from substantially diametrically opposite sides of outlet 28. Wings 30 and 32 are flexible relative to outlet 28 and can be urged into substantially abutting face-to-face relationship with one another to facilitate gripping and maneuvering of catheter hub 16 during insertion of the catheter into a patient. Alternatively, wings 30 and 32 can be urged into a substantially coplanar orientation as shown in FIGS. 1 and 5 for taping catheter hub 16 in a fixed position on a patient. First inlet 24 of fitting 16 defines an inside diameter "D" which is equal to or slightly less than outside diameter "C" of rigid plug retainer 14.

Plug assembly 10 is assembled into the condition shown in FIG. 5 by initially compressing plug 12 radially approximately 15% to 40%, preferably 30%, so that the outside diameter of plug 12 is reduced approximately to dimension "B". This compression of plug 12 may be simultaneous along the length thereof or may be gradual, beginning at one end and continuing to the other. Plug 12, in its compressed condition, is then inserted into the central aperture of plug retainer 14, such that inner circumferential surface 20 of plug retainer 14 securely engages outer circumferential surface 18 of plug 12 along at least a major portion of the respective lengths. Thus, plug retainer 14 securely retains plug 12 in a state of radial compression where plug 12 defines a diameter equal to approximately 70% of its initial non-compressed diameter.

The subassembly of plug 12 and plug retainer 14 is then inserted into inlet 24 of catheter hub 16. This insertion requires an outward stretching of the elastomeric material of inlet 24. However, the elastomeric material of inlet 24 is resiliently urged toward an unbiased condition, and hence securely grips the subassembly comprising plug 12 and plug retainer 14 in catheter hub 16.

Plug assembly 10 may be used in the conventional manner by inserting a needle 34 approximately axially through plug 12 for communication with a patient. Needle 34 may be removed when necessary and may be replaced with a new needle. Removal of needle 34 from plug 12 permits the elastic material of plug 12 to return toward an unbiased condition in which the cylindrical aperture that had been occupied by needle 34 is substantially filled. This sealing of plug 12 after removal of needle 34 is positively assured by the radial compression of plug 12 achieved and maintained by plug retainer 14.

Thus, it is seen that needles may be passed through the compressed elastic plug in the conventional manner, and may be removed and reinserted as necessary. The retention of the elastic plug in the compressed state by the rigid plug retainer ensures that the elastic material of the plug will not take a permanent set to the needle, even when the needle has been in the elastic plug for a considerable time. Thus, the radially compressed elastic material of the plug will resiliently return toward a less compressed condition when the needle is removed to completely fill the space that had been occupied by the needle. New needles may be, penetrated through the elastic plug and may be removed without adversely affecting the sealing capabilities of the plug. Additionally, the radial compression of the elastic plug has no practical effect on the ability of a health care worker to urge the needle through the plug.

What is claimed is:

1. A medical device, comprising:

an inlet formed from an elastic material;

a rigid plug retainer disposed in the inlet, the rigid plug retainer being radially compressed and surrounded by the elastic material of the inlet to prevent longitudinal movement of the rigid plug retainer; and a compressible elastic plug disposed in the rigid plug retainer, the compressible elastic plug being radially compressed and surrounded by the rigid plug retainer to ensure that any hole in the compressible elastic plug caused by a needle being inserted therein is substantially closed after the needle is withdrawn.

2. The medical device of claim 1 wherein said compressible elastic plug is compressed to a second cross-sectional dimension equal to between 60%–85% of a first cross-sectional dimension of said compressible elastic plug in an unbiased state.

3. The medical device of claim 2, wherein said compressible elastic plug is compressed so the second cross-sectional dimension is equal to approximately 70% of the first cross-sectional dimension of said compressible elastic plug in said unbiased state.

* * * * *